United States Patent [19]

Sonoi et al.

[11] Patent Number: 5,672,742

[45] Date of Patent: Sep. 30, 1997

[54] PROCESS FOR PRODUCING α-(TRIFLUOROMETHYL)ARYLACETIC ACID

[75] Inventors: Takehiro Sonoi, Kitaibaraki, Japan; Futoshi Masaki, deceased, late of Hitachi, Japan, by Toshio Kubota, legal representative; Toshio Kubota, Hitachi, Japan

[73] Assignee: Nippon Mektron Limited, Tokyo, Japan

[21] Appl. No.: 615,557

[22] Filed: Mar. 12, 1996

[30] Foreign Application Priority Data

Jun. 8, 1995 [JP] Japan ................................ 7-166967

[51] Int. Cl.$^6$ ................................................. C07C 53/34
[52] U.S. Cl. ............................................................. 562/496
[58] Field of Search ............................................... 562/496

[56] References Cited

PUBLICATIONS

Aaron et al., "Resolution and Configuration of α–Substituted Phenylacetic Acids" *Journal of Organic Chemistry*, vol. 32, pp. 2797–2803 (1967).

Middleton et al., "The Synthesis of Antiinflammatory α–(Triflouromethyl)Arylacetic Acids", *Journal of Fluorine Chemistry*, vol. 22, pp. 561–574 (1983).

Everett et al., "Preparation of α–Trifluoromethyl Esters From Malonic Esters", *Journal of Organic Chemistry*, vol. 49, pp. 3702–3706 (1984).

Muzard et al., "Fluorinated Ketene Dithioacetals; 1, Preparation and Application to the Synthesis of α–Trifluoromethylthiocarboxylic S–Esters and Aldehyde Derivatives", *Synthesis*, vol. pp. 965–968 (1992).

No. 69 Spring Annual Meeting Preprints II, pp. 1080 of Chemical Society of Japan, Mar. 13, 1995 [Issn 0285–7626].

*Primary Examiner*—Paul J. Killos

[57] ABSTRACT

α-(trifluoromethyl)arylacetic acid for use as raw materials for medicines, agricultural chemicals, liquid crystals etc. or reagents for determining an optical purity is readily obtained through very simple reaction steps, i.e. by reacting a perfluoro(2-methyl-1,2-epoxypropyl)ether compound obtainable by ozone, oxidation of a heptafluoroisobutenyl ether compound with an aromatic compound ArH to afford an α,α-bis(trifluoromethyl)arylacetic acid ester, followed by decarboxylation and hydrolysis of the resulting ester compound.

5 Claims, No Drawings

PROCESS FOR PRODUCING α-(TRIFLUOROMETHYL)ARYLACETIC ACID

BACKGROUND OF THE INVENTION

1. Field of the Invention

The present invention relates to a process for producing α-(trifluoromethyl)arylacetic acid, and more particularly to a process for producing α-(trifluoromethyl)arylacetic acid for use as raw materials for medicines, agricultural chemicals, liquid crystals, etc. or reagents for determining an optical purity, etc.

2. Related Prior Art

α-(trifluoromethyl)arylacetic acid represented by the following general formula:

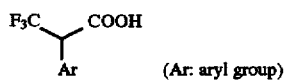

(Ar: aryl group)

can be produced according to the following conventional procedures:

(1) Journal of Organic Chemistry, vol. 32, page 2797 (1967)

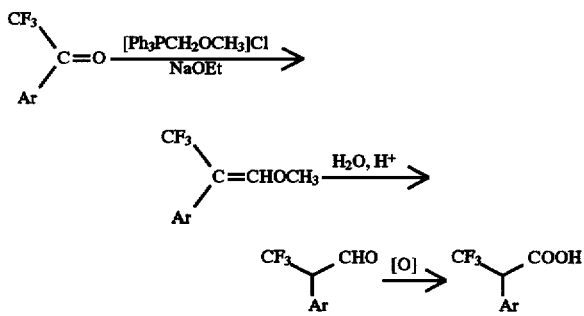

(2) Journal of Fluorine Chemistry, vol. 22, page 561 (1983)

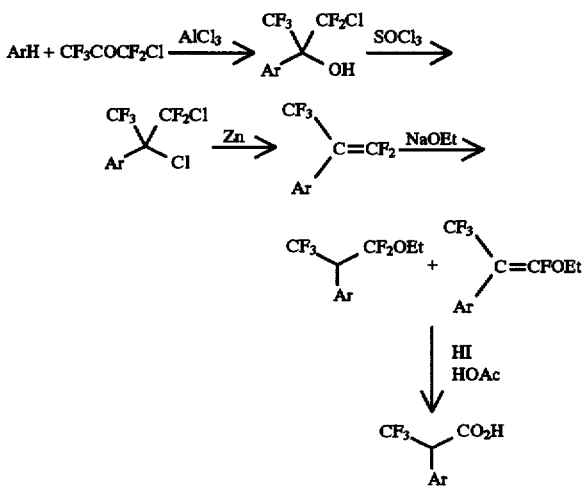

(3) Journal of Organic Chemistry, vol. 49, page 3702 (1984)

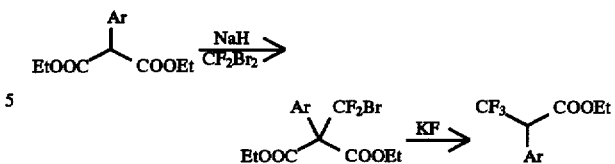

(4) Synthesis, vol. 10, page 965 (1992)

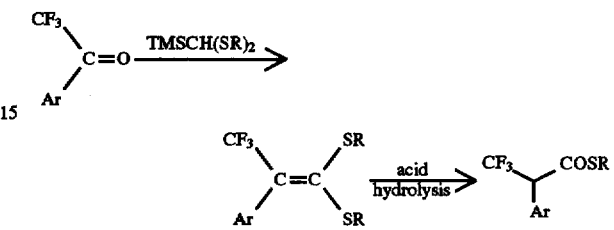

However, these procedures are not economically advantageous owing to expensive starting materials, necessity for a plurality of synthesis steps, difficulty in mass-production, etc.

SUMMARY OF THE INVENTION

An object of the present invention is to provide a process economically producing α-(trifluoromethyl)arylacetic acid for use as law materials for medicines, agricultural chemicals, liquid crystals, etc. or reagents for determining an optical purity, etc.

DETAILED DESCRIPTION OF THE INVENTION

According to the present invention, the desired α-(trifluoromethyl)arylacetic acid, represented by the following general formula:

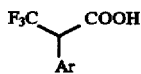

wherein Ar is an aryl group, can be produced by reaction of an α,α-bis(trifluoromethyl)arylacetic acid ester, represented by the following general formula:

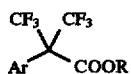

where Ar has the same meaning as defined above; R is a lower alkyl group, an aryl group or a benzyl group, with a base in the presence of water.

α,α-bis(trifluoromethyl)arylacetic acid ester, represented by the following general formula:

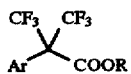

can be obtained by the reaction of a perfluoro(2-methyl-1,2-epoxypropyl)ether compound, represented by the following general formula as a starting material:

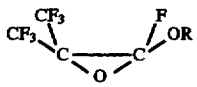

with an aromatic compound ArH.

Perfluoro(2-methyl-1,2-epoxypropyl)ether compound as the starting material can be prepared by oxidation of a heptafluoroisobutenyl ether compound, represented by the general formula $(CF_3)_2C=CF(OR)$, with ozone, and heptafluoroisobutenyl ether compound as a starting material for it can be readily obtained by addition reaction of octafluoroisobutene $(CF_3)_2C=CF_2$ with a lower alcohol, phenol, benzyl alcohol or the like, followed by dehydrofluorination reaction of the resulting addition reaction product $(CF_3)_2CHCF_2OR$ with potassium hydroxide or the like.

The oxidation reaction of heptafluoroisobutenyl ether compound with ozone is carried out in a glass reactor by charging the starting material and contacting it with an ozone-containing oxygen gas or air in the absence of a solvent or in the presence of such a solvent as hydrocarbon, halogenated hydrocarbon, ether or water with stirring at a temperature of about −70° C. to about 110° C., preferably about −40° C. to about 60° C. Ozone concentration in oxygen gas or air is not particularly limited, but generally is about 0.1 to about 1,000 mg/liter, preferably about 1 to 500 mg/liter. Molar ratio of ozone to the starting material for the oxidation reaction is about 1.

Epoxy group of the resulting perfluoro(2-methyl-1,2-epoxypropyl)ether compound has a very high activity and undergo cleavage easily in the presence or absence of a catalyst to react with an aromatic compound ArH, thereby forming an α,α-bis(trifluoromethyl)arylacetic acid ester.

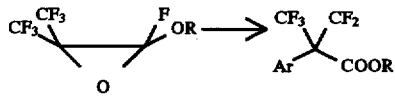

The aromatic compound ArH for this purpose includes, for example, aromatic hydrocarbons such as benzene, naphthalene, etc. and aromatic heterocyclic compounds such as pyrrole, pyridine, etc. and may have a lower alkyl group such as methyl, ethyl, isopropyl, t-butyl, etc. or a halogen such as chlorine, bromine, etc. as a substituent. The aromatic compound is used in large excess over the ether compound, generally in a molar ratio of the aromatic compound to the ether compound of about 1 to about 100, preferably about 1 to about 40.

The reaction of the ether compound with the aromatic compound is carried out in the presence or absence of a solvent. In the case of using a solvent, the species of the solvent is not limited, so long as it is inert to the ether compound and the aromatic compound, but it is preferable to use a solvent having a higher dissolvability. When an aromatic hydrocarbon is used as the aromatic Compound in the reaction, it is preferable to use a catalyst. Preferable catalyst includes, for example, such Lewis acids as $AlCl_3$, $AlBr_3$, $ZnI_2$, $TiCl_4$, $SnCl_4$, $BF_3$, etc. The catalyst is used in a molar ratio of the catalyst to the ether compound of about 0.01 to about 10, preferably about 0.1 to about 3. The reaction temperature for this purpose is about −80° C. to about 200° C., preferably about −40° C. to about 100° C.

The resulting α,α-bis(trifluoromethyl)arylacetic acid ester can be converted to α-(trifluoromethyl)arylacetic acid by reaction with a base in the presence of water.

The base for use in the conversion includes, for example, alkali metal hydroxides such as sodium hydroxide, potassium hydroxide, etc., and alkaline earth metal hydroxides such as calcium hydroxide, magnesium hydroxide, etc. Preferable is the alkali metal hydroxide. When the base is an alkali metal hydroxide, it is used in a molar ratio of it to the ester compound of about 1 to about 10, and water is used in a proportion of about 100 to about 10,000 ml, preferably about 500 to about 3,000 ml per mole of the ester compound.

When an alcohol such as methanol, ethanol, n-propanol, isopropanol, etc. is added to the reaction system during the reaction, the reaction system can be kept in a homogeneous phase, thereby promoting the reaction. The reaction temperatures is generally about −40° C. to about 150° C., preferably about −20° C. to about 100° C.

α,α-bis(trifluoromethyl)arylacetic acid ester is converted to the corresponding carboxylic acid salt under the action of the base and water, followed by decarboxylation to form an olefinic compound, and further by hydrolysis to form an α-(trifluoromethyl)arylacetic acid, as schematically given belows.

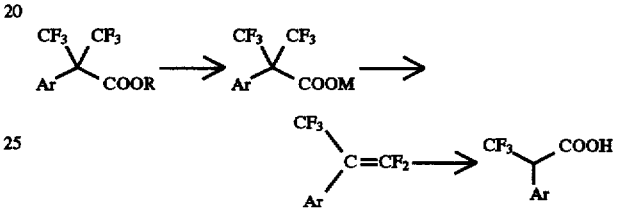

α-(trifluoromethyl)arylacetic acid can be readily produced through very simple reaction steps, that is by subjection a perfluoro(2-methyl-1,2-epoxypropyl)ether compound, which can be obtained by oxidation of heptafluoroisobutenyl ether compound with ozone, to reaction with an aromatic compound, thereby obtaining an α,α-bis(trifluoromethyl) arylacetic acid ester, followed by decarboxylation and hydrolysis.

PREFERRED EMBODIMENTS OF THE INVENTION

The present invention will be explained in detail below, referring to Examples and Reference Examples.

REFERENCE EXAMPLE 1

200 g (0.88 moles) of heptafluoroisobutenyl methyl ether (purity: 93%) was charged into a three-necked flask having a capacity of 300 ml, provided with a Dimroth condenser, a stirrer and a gas feed tube, and a brine at −20° C. was passed through the Dimroth condenser. About 340 liters of ozone-containing oxygen gas (ozone concentration: 125 mg/liter) was bubbled through the ether Compound at 0° C. with stirring over 11 hours 18 minutes (total ozone amount: about 0.88 moles). After the reaction, 134.8 g of the reaction product was recovered therefrom and distilled, whereby 73.0 g of perfluoro(2-methyl-1,2-epoxypropyl) methyl ether was obtained as a fraction having a boiling point of 82° to 85° C. (yield: 36.5%).

Infrared absorption spectrum: 1230 $cm^{-1}$ (oxirane ring)

$^{19}$F-NMR (TFA, $CH_2Cl_2$): −15.3 ppm (d, J=2.19 Hz, 1F)

+0.58 ppm (dq, J=2.19, 2.63 Hz, 3F)

+1.90 ppm (q, J=2.63 Hz, 3F)

$^1$H-NMR (TMS, $CDCl_3$): 3.58 ppm (s, 3H)

Mass spectrum (EI, M/Z): 228($M^+$)

REFERENCE EXAMPLE 2

6.67 g of anhydrous aluminum chloride and 50 ml of dry benzene were charged into a three-necked flask having a capacity of 300 ml, provided with a stirrer and a dropping funnel, and the flask was cooled to 0° C. Then, 11.4 g (0.05 moles) of perfluoro(2-methyl-1,2-epoxypropyl) methyl ether diluted with 30 ml of dry benzene was dropwise added into the flask with stirring. Reaction was carried out at room temperature for 10 hours while stirring, and then the reaction mixture was poured into ice water, and the separated organic layer was dried with anhydrous $MgSO_4$. The aqueous layer was extracted with dichloromethane, and the liquid extract was dried with anhydrous $MgSO_4$. These two organic layers were joined together and concentrated, and then the residue was distilled at a bath temperature of 120° to 130° C. under reduced pressure of 15 mmHg, whereby 10.05 g of methyl ester of α,α-bis(trifluoromethyl)phenylacetic acid was obtained (yield: 70%).

Infrared absorption spectrum: 1810 cm$^{-1}$ (C═O)

$^{19}$F-NMR (TFA, $CH_2Cl_2$): +4.1 ppm (s)

$^1$H-NMR (TMS, $CDCl_3$): 3.7 ppm (s, 3H)

7.1 ppm (m, 5H)

REFERENCE EXAMPLE 3

2.67 g of anhydrous aluminum chloride and 10 ml of dry isobutylbenzene were charged into a three-necked flask having a capacity of 50 ml, provided with a stirrer and a dripping funnel, and then the flask was cooled to 0° C. Then, 4.56 g (0.02 moles) of perfluoro(2-methyl-1,2-epoxypropyl) methyl ether diluted with 2 ml of dry isobutylbenzene was dropwise added into the flask with stirring. Reaction was carried out at room temperature for 10 hours, while stirring, and the reaction mixture was poured into ice water, and the separated organic layer was dried with anhydrous $MgSO_4$. The aqueous layer was extracted with dichloromethane and the liquid extract was dried with anhydrous $MgSO_4$. These two organic layers were joined together and concentrated. Then, the residue (10.98 g) was distilled at a bath temperature of 40° to 120° C. under reduced pressure of 5 mmHg, and the thus obtained fraction was subjected to silica gel column chromatography, using n-hexane as a mobile phase, whereby 4.05 g of methyl ester of α,α-bis(trifluoromethyl)-p-isobutylphenylacetic acid was obtained (yield: 59%).

Infrared absorption spectrum: 1790 cm$^{-1}$ (C═O)

$^{19}$F-NMR (TFA, $CH_2Cl_2$): −3.2 ppm (s)

$^1$H-NMR (TMS, $CDCl_3$): 0.87 ppm (d, J=7.2 Hz, 6H)

1.35 to 2.34 ppm (m, 1H)

2.43 ppm (d, J=6.3 Hz, 2H)

3.81 ppm (s, 3H)

7.02 ppm (s, 4H)

REFERENCE EXAMPLE 4

1.28 g (0.01 mole) of naphthalene, 50 ml of dry dichloromethane and 2.28 g (0.01 mole) of perfluoro(2-methyl-1,2-epoxypropyl) methyl ether were charged into a three-necked flask having a capacity of 100 ml, provided with a stirrer and a dropping funnel, and the flask was cooled to 0° C. Then, 1.23 ml of $BF_3.Et_2O$ was added into the flask with stirring. Reaction was carried out at 45° C. for 24 hours while stirring, and then the reaction mixture was poured into ice water, and the separated organic layer was dried with anhydrous $MgSO_4$. The aqueous layer was extracted with dichloromethane and the liquid extract was dried with anhydrous $MgSO_4$. These two organic layers were joined together and concentrated, and then the residue (2.86 g) was sublimated at a bath temperature of 60° to 120° C. under reduced pressure of 20 mmHg, whereby 1.47 g of the sublimate was obtained. The sublimate was then subjected to silica gel column chromatography, using n-hexane/ dichloromethane as a mobile phase, whereby 0.84 g of methyl ester of α,α-bis(trifluoromethyl)naphthylacetic acid was obtained (yield: 25%).

Infrared absorption spectrum: 1800 cm$^{-1}$ (C═O)

$^{19}$F-NMR (TFA, $CH_2Cl_2$): −5.3 ppm (s)

$^1$H-NMR (TMS, $CDCl_3$): 3.82 ppm (s, 3H)

6.90 to 8.20 ppm (m, 7H)

REFERENCE EXAMPLE 5

0.67 g (0.01 mole) of pyrrole was charged into a three-necked flask having a capacity of 10 ml, provided with a stirrer and a dropping funnel, and the flask was cooled to 0° C. Then, 2.28 g (0.01 mole) of perfluoro(2-methyl-1,2-epoxypropyl) methyl ether was dropwise added into the flask with stirring. After the dropwise addition, dichloromethane and water were added thereto with Stirring and in that state the aqueous layer was neutralized with sodium hydrogen carbonate. The separated organic layer was dried with anhydrous $MgSO_4$. These two organic layers were joined together and concentrated, and the residue (0.97 g) was subjected to silica gel column chromatography, using n-hexane as a mobile phase, whereby 0.3 g of methyl ester of α,α-bis(trifluoromethyl)-2-pyrrolylacetic acid was obtained (yield: 10%).

Infrared absorption spectrum: 1740 cm$^{-1}$ (C═O)

3435 cm$^{-1}$ (NH)

$^{19}$F-NMR (TFA, $CH_2Cl_2$): −1.0 ppm (s)

$^1$H-NMR (TMS, $CDCl_3$): 3.46 ppm (s, 3H)

6.05 to 7.14 ppm (m, 3H)

7.76 to 9.34 ppm (br, 1H)

EXAMPLE 1

2.9 g (10 millimole) of methyl ester of α,α-bis (trifluoromethyl)phenylacetic acid obtained in Reference Example 2, 2.5 g (63 millimole) of sodium hydroxide, 3.0 g of water and 3.0 ml of methanol were charged into an eggplant-type flask having a capacity of 100 ml, provided with a marine-type condenser and refluxed at a bath temperature of 90° C. for 6 hours. Methanol was distilled off from the reaction mixture under reduced pressure, and the residue was dissolved in 30 ml of 3N hydrochloric acid and then extracted with ether. The ether layer was dried with anhydrous $MgSO_4$ and then concentrated under reduced pressure. The thus obtained residue was subjected to silica gel column chromatography, using n-hexane/ dichloromethane as a mobile phase, whereby 1.26 g of α-(trifluoromethyl) phenylacetic acid was obtained (yield: 62%).

Infrared absorption spectrum: 3210 cm$^{-1}$ (OH)

1720 cm$^{-1}$ (C═O)

$^{19}$F-NMR (TFA, $CH_2Cl_2$): −1.29 ppm (d, J=7.6 Hz)

$^1$H-NMR (TMS, $CDCl_3$): 4.26 ppm (q, 1H, J=7.2 Hz, methine-H)

7.28 ppm (s, 5H, ph)

11.9 ppm (br, 1H, OH)

Mass spectrum (CI, M/Z): 205(M$^+$+1)

EXAMPLE 2

Reaction was carried out in the same manner as in Example 1, except that methyl ester of α,α-bis (trifluoromethyl)-p-isobutylphenylacetic acid obtained in Reference Example 3 was used in place of methyl ester of α,α-bis(trifluoromethyl)phenylacetic acid obtained in Reference Example 2, whereby α-(trifluoromethyl)-p-isobutylphenylacetic acid was obtained in yield of 43%.

What is claimed is:

1. A process for producing α-(trifluoromethyl)arylacetic acid, represented by the following general formula:

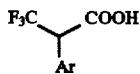

wherein Ar is an aryl group, which comprises subjecting an α,α-bis(trifluoromethyl)arylacetic acid ester, represented by the following general formula:

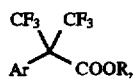

wherein Ar has the same meaning as defined above and R is a lower alkyl group, an aryl group or a benzyl group, to reaction with a base in the presence of water.

2. A process according to claim 1, wherein the α,α-bis(trifluoromethyl)arylacetic acid ester is methyl ester of α,α-bis(trifluoromethyl)phenylacetic acid.

3. A process according to claim 1, wherein the α,α-bis(trifluoromethyl)arylacetic acid ester is methyl ester of α,α-bis(trifluoromethyl)-lower alkyl-substituted phenylacetic acid.

4. A process according to claim 1, wherein the base is an alkali metal hydroxide or an alkaline earth metal hydroxide.

5. A process according to claim 1, wherein the reaction is carried out in the presence of an alcohol.

* * * * *